(12) United States Patent
Kappel et al.

(10) Patent No.: US 9,592,036 B2
(45) Date of Patent: Mar. 14, 2017

(54) MULTI-FUNCTIONAL TISSUE MANIPULATION MEDICAL DEVICE AND RELATED METHODS OF USE

(71) Applicant: Boston Scientific Scimed, Inc., Maple Grove, MN (US)

(72) Inventors: Gary Kappel, Acton, MA (US); Sean Fleury, Marlborough, MA (US); Paul Smith, Smithfield, RI (US); Brandon Zalewski, Clinton, MA (US); Laurie Soderbom, Nashua, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 533 days.

(21) Appl. No.: 13/944,624

(22) Filed: Jul. 17, 2013

(65) Prior Publication Data
US 2014/0046320 A1    Feb. 13, 2014

Related U.S. Application Data

(60) Provisional application No. 61/680,971, filed on Aug. 8, 2012.

(51) Int. Cl.
*A61B 17/221* (2006.01)
*A61B 18/14* (2006.01)
(Continued)

(52) U.S. Cl.
CPC .... *A61B 17/00234* (2013.01); *A61B 17/3205* (2013.01); *A61B 17/32056* (2013.01); *A61B 18/1482* (2013.01); *A61B 18/1492* (2013.01); *A61B 17/221* (2013.01); *A61B 18/20* (2013.01); *A61B 2017/00353* (2013.01); *A61B 2017/2215* (2013.01); *A61B 2017/22034* (2013.01); *A61B 2017/320064* (2013.01);
(Continued)

(58) Field of Classification Search
CPC ............ A61B 17/00234; A61B 17/221; A61B 17/3205; A61B 17/32056; A61B 2017/00353; A61B 2017/22034; A61B 2017/2215; A61B 2017/320064; A61B 18/1482; A61B 18/1492; A61B 18/20; A61B 2018/00267; A61B 2018/00595; A61B 2018/141; A61B 2018/1422; A61B 2018/144; A61B 2019/5466
USPC ...................................................... 606/41–52
See application file for complete search history.

(56) References Cited

U.S. PATENT DOCUMENTS

| | | | | |
|---|---|---|---|---|
| 5,197,968 A | * | 3/1993 | Clement | A61B 17/221 |
| | | | | 604/119 |
| 5,578,030 A | * | 11/1996 | Levin | A61B 10/0233 |
| | | | | 606/39 |

(Continued)

*Primary Examiner* — Michael Peffley
*Assistant Examiner* — Khadijeh Vahdat
(74) *Attorney, Agent, or Firm* — Bookoff McAndrews, PLLC

(57) ABSTRACT

A multi-functional medical device including a sheath having a proximal end, a distal end, and a lumen extending between the proximal end and the distal end. The medical device further includes an end-effector slidably disposed within the lumen. A portion of the end-effector may be configured to transition between a collapsed state while in the lumen and an expanded state while out of the lumen. Further, the end-effector may include a tool configured to dissect tissue, and a retracting member having a plurality of legs disposed about the tool.

19 Claims, 10 Drawing Sheets

(51) Int. Cl.
    *A61B 17/00*       (2006.01)
    *A61B 17/3205*    (2006.01)
    *A61B 17/32*       (2006.01)
    *A61B 18/20*       (2006.01)
    *A61B 17/22*       (2006.01)
    *A61B 18/00*       (2006.01)

(52) U.S. Cl.
    CPC ........... *A61B 2018/00267* (2013.01); *A61B 2018/00595* (2013.01); *A61B 2018/141* (2013.01); *A61B 2018/144* (2013.01); *A61B 2018/1422* (2013.01); *A61B 2090/3966* (2016.02)

(56) References Cited

U.S. PATENT DOCUMENTS

| | | | | |
|---|---|---|---|---|
| 5,782,899 | A * | 7/1998 | Imran | A61B 18/1492 600/374 |
| 6,063,082 | A * | 5/2000 | DeVore | A61B 17/3468 606/170 |
| 2002/0120254 | A1* | 8/2002 | Julian | A61B 17/00234 606/1 |
| 2005/0096647 | A1* | 5/2005 | Steinke | A61B 18/1492 606/41 |
| 2008/0097422 | A1* | 4/2008 | Edwards | A61B 18/12 606/34 |

* cited by examiner

MULTI-FUNCTIONAL TISSUE MANIPULATION MEDICAL DEVICE AND RELATED METHODS OF USE

CROSS-REFERENCE TO RELATED APPLICATIONS

This application claims the benefit of priority from U.S. Provisional Application No. 61/680,971, filed on Aug. 8, 2012, the entirety of which is incorporated by reference herein.

FIELD OF THE INVENTION

Embodiments of the present disclosure relate generally to medical devices suitable for use in surgical procedures. In particular, embodiments of the present disclosure relate to minimally invasive multi-functional medical devices employed for body tissue manipulation.

BACKGROUND OF THE INVENTION

Minimally invasive medical procedures typically involve introducing certain instruments, such as endoscopic devices or catheters, into a patient's body through natural body openings or through percutaneous incisions. These instruments may then be urged distally through cavities in the body to a desired site. At the location, various medical devices, such as suction pumps, cauterization tools, graspers, clippers, lasers, baskets, lithotripters, forceps, biopsy devices, or snares, may be inserted through the introducers, e.g., catheters or endoscopic devices, allowing operators to perform procedures within the patient's body without causing massive trauma.

For these procedures, multiple devices are sometimes required. For example, for a polyp dissection procedure, a dissection tool, such as a cautery hook, and a retraction device may be required. Surgeons may insert a cautery hook, e.g., into the patient's body to dissect tissue. Subsequently, the cautery hook may be retracted and replaced by a retraction device. Changing devices during the procedure, however, may inadvertently change the location of the distal end of the endoscopic device. Excessive time is then required to determine the original location and retract the dissected tissue. If the operator cannot find the exact location, the dissected tissue may remain within the patient's body, increasing the likelihood of infection. Further, replacing and relocating devices may increase procedure time and, therefore, procedure cost.

Thus, there exists a need to minimize the need to exchange devices, allowing operators to conduct safer, quicker, and more efficient medical procedures.

SUMMARY OF THE INVENTION

Embodiments of the present disclosure relate to a multi-function device for carrying out minimally invasive procedures within a patient's body.

One embodiment of the present disclosure is directed to an end-effector for a medical device. The end-effector may include a cauterization tool, and a retracting member having a proximal end, a distal end, and plurality of legs extending from the proximal end to the distal end such that the proximal and distal ends of the legs are joined together. The plurality of legs may be capable of translating between a collapsed configuration and an expanded configuration.

In various embodiments, the end-effector may include one or more of the following additional features: the distal end of the end-effector may include an atraumatic tip; an inward-facing surface of one or more of the legs may include one or more projections; an outward-facing surface of one or more of the legs may include one or more projections; the medical device may include an elongate member defining a lumen for receiving the end-effector; both of the proximal and distal ends may be joined together; and the retracting member may be self-expandable.

Another embodiment of the present disclosure is directed to a multi-functional medical device including a sheath having a proximal end, a distal end, and a lumen extending between the distal and proximal ends. The device may further include an end-effector slidably disposed within the lumen. A portion of the end-effector may be configured to transition between a collapsed state while in the lumen and an expanded state while out of the lumen. The end-effector may include a tool configured to dissect tissue and a retracting member having one or more legs disposed about the tool.

In various embodiments, the multi-function device may include one or more of the following additional features: the tool may be a cautery hook; the retracting member may be a basket; the basket may be self-expandable; the legs may be coupled at a distal end and a proximal end of the retracting member, and a middle portion of the legs may expand radially in the expanded state; when in the expanded state, a distal portion of the legs may expand radially; when in the expanded state, a proximal portion of the legs may expand radially; the tool may include a snare; a plurality of projections may be disposed on a surface of the legs; a distal end of the retracting member may include an atraumatic tip; the retracting member may include a mesh; and each of the plurality of legs of the retracting member includes a proximal end and a distal end, and only one of the proximal and distal ends of the plurality of legs are coupled together.

In another embodiment, the present disclosure is directed to a method for manipulating tissue within a body of a patient. The method may include the step of introducing a medical device into the body. The medical device may include an end-effector. A portion of the end-effector may be configured to transition between a collapsed state and an expanded state. The end-effector may include a tool configured to dissect tissue and a retracting member having a plurality of legs disposed about the cutting tool. The method may further include the steps of advancing the medical device to a desired location within the body, expanding the retracting member, excising tissue within the body of the patient with the tool, and collapsing the retracting member to manipulate the excised tissue.

BRIEF DESCRIPTION OF THE DRAWINGS

The accompanying drawings, which are incorporated in and constitute a part of this specification, illustrate embodiments of the invention and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts.

Overview

Embodiments of the present disclosure are directed to integrated medical tools for endoscopic devices. The integrated medical tools form a single device that may perform two or more medical functions. Exemplary integrated medical devices may include a dissection tool, such as a cautery hook, a laser ablation tool, a lithotripter, a snare loop, a surgical clipper, a blade, a scraper, or scissors; and a retraction member, such as an expandable basket, a mesh, a funnel, graspers, forceps, or pincers. Further, the integrated device may include any other combination of medical devices suitable for use in a surgical procedure, without departing from the scope of the present disclosure.

In this disclosure, embodiments are described using an integrated medical device comprising a cautery hook and an expandable retracting device capable of transitioning between an expanded state and a compressed state. It will be understood, however, that the device and method may be incorporated in a similar device, such as a snare loop and grasper combination, scissors, or a laser fiber and a mesh combination, without departing from the scope of the present disclosure.

In the described embodiments, the expandable retracting member accomplishes at least two functions. First, in its compressed state, it retracts tissue dissected by the cauterization tool and may shield the hook for safe and easy passage through a working channel or a body lumen. Second, in its expanded state, it may increase the cavity size by pushing outwardly on the tissue surrounding the cauterization tool. The shield therefore may be configured to provide the cautery tool with the space necessary to cauterize the desired tissue without harming any neighboring tissue.

As used throughout this disclosure, "cauterization tool" refers to a suitable medical device that cauterizes body tissue during a dissection procedure. Further, "retracting member" refers to a suitable device that moves or manipulates tissue, for example, to gain access to a targeted site and/or removes dissected tissue material from a patient's body, for example, after a cauterization procedure. Exemplary retracting members may include, for example, a basket, malecot, snare, net, paddle, fan, spreader, and funnel.

Exemplary Embodiments

Figure 1A:
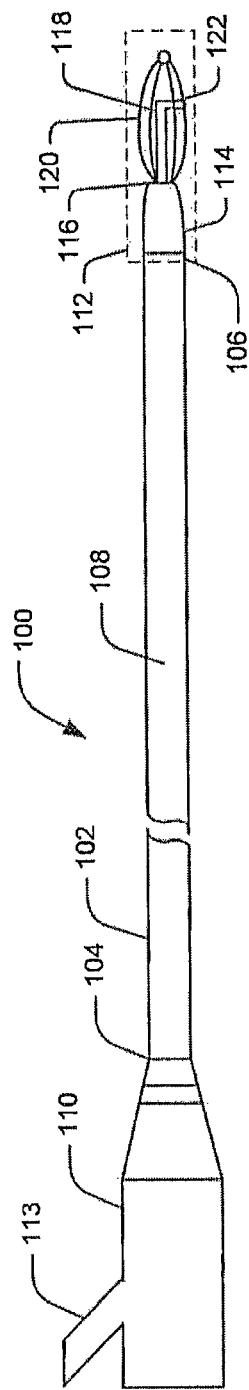
FIG. 1A is a schematic side view of an exemplary integrated medical device according to embodiments of the present disclosure.

FIG. 1A illustrates an exemplary integrated medical device 100 according to embodiments of the present disclosure. The device includes an elongate sheath 102 having a proximal end 104, a distal end 106, and lumen 108 formed in between. Medical device 100 further includes a handle 110 coupled to the sheath's proximal end 104 and an end-effector 112 coupled to its distal end 106.

Sheath 102 may include a substantially circular cross-section or at least a partially circular cross-section. Sheath 102 may be made of a suitable biocompatible material, such as polyurethane, polytetrafluoroethylene, plastic, or other such materials. Other suitable cross-sectional shapes may include, e.g., elliptical, oval, polygonal, or irregular shapes. In some embodiments, sheath 102 may include a coiled or braided structure. Moreover, sheath 102 may have a uniform configuration or may vary along its length. For example, the distal tip of sheath 102 may be smooth, rounded, and/or tapered for convenient delivery. In some embodiments, an inner and/or an outer surface of sheath 102 may be substantially smooth. Alternatively, an inner and/or outer surface may be textured, for example, there may be grooves, ridges, bumps, protrusions or any other suitable surfacing. In some embodiments, sheath 102 may include a coating or outer layer, for instance, a lubricious coating, an antibacterial coating, or a soft and/or deformable outer layer to protect against injury or puncture when inserted in a patient.

Moreover, sheath 102 may be flexible along its entire length, or adapted for flexure along portions of its length. In some embodiments, the distal end 106 may be flexible, while the remainder of sheath 102 may be rigid. In some embodiments, sheath 102 may exhibit variable stiffness at one or more points along its length or at its ends. Flexibility may allow sheath 102 to maneuver circuitous turns in the patient's body, while rigidity may provide the necessary force to urge device 100 forward. Moreover, the distal end of the sheath may be steerable, allowing an operator to accurately position the sheath within a patient's body. Steering means, such as mechanical or electrical actuators, may be present on the handle. Sheath steering means, such as pull wires, are widely known in the art, and any of these means may be utilized without departing from the scope of the present disclosure.

A lubricious coating may be applied to the outer surface of sheath 102 to facilitate insertion in a body lumen or an endoscopic device. Further, to detect the position of sheath 102 within a patient's body, at least some portions of sheath 102 may include radiopaque materials or markers, such as gold, palladium, platinum, tantalum, tungsten alloy, or polymeric materials loaded with radiopaque agents, such as barium sulfate ($BaSO_4$) or bismuth subcarbonate (($BiO)_2CO_3$). Radiopaque materials are understood to be materials capable of producing a relatively bright image on a fluoroscopic monitor or other imaging device. In some embodiments, reinforcing coils, braids, or other structural components may be radiopaque.

Sheath 102 and end-effector 112 may be coated with an antibacterial covering to inhibit bacterial growth on their surfaces. The antibacterial coating may contain an inorganic antibiotic agent, disposed in a polymeric matrix that adheres the antibiotic agent to the sheath and end-effector surfaces. Further, a drug-releasing coating may also be applied to the outer surface, to assist in drug delivery to the target site.

Lumen 108 may include one or more working channels (not shown) extending from proximal end 104 to distal end 106. Operators may insert different medical devices within the working channels. For example, an operator may place a cauterization tool in one channel and a retraction device in another. More than one tool or device may be also be inserted through a single channel, as desired. It is understood that other exemplary tools may also be inserted into the working channels without departing from the scope of the present disclosure.

Handle 110 may allow operators to grip the medical device for manipulation within the patient's body. Handle 110 may assume any suitable desired shape, such as ring, spool, etc. In some embodiments, handle 110 may include a polymer grip coating for effective handling. Further, handle 110 may include one or more ports 113 for inserting tools into medical device 100. Ports 113 may also be used to connect certain medical devices to external power sources, if required. To this end, ports 113 may include electrical connections. Alternatively, if the tools are prefixed within sheath 102, and no external connections are required, the handle may not include external ports 113. In addition to ports, handle 110 may also include, for example, maneuvering means to navigate distal end 106 of sheath 102 within a patient's body. Such means may include mechanical levers, sliders, or pulleys; electronic buttons, switches, or joysticks; or a combination of mechanical and electronic controls. Further, handle 110 may include control means to actuate end-effector 112 between a first and second position. For example, end-effector 112 may be translatable between a deployed position and a rest position. In the rest position, end-effector 112 may lie within sheath 102, and in the deployed position, it may extend distally beyond distal end 106. In some embodiments, sheath 102 may be retractable to cause deployment and/or retraction in end-effector 112.

Handle 110 may be temporarily or permanently attached to proximal end 104. Various temporary and permanent attachment means exist, such as snap-fit, screw-fit, luer-lock, gluing, welding, etc. Any such means may be utilized without departing from the scope of the present disclosure.

Figure 1B:
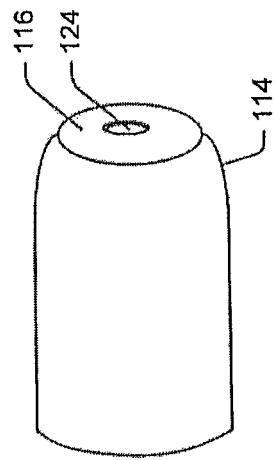
FIG. 1B is a schematic perspective view of an exemplary distal end of the device of FIG. 1A.

FIG. 1B is a schematic illustrating an exemplary embodiment of end-effector 112, which may include a cap-like structure 114 with a base 116, and at least two tools configured to extend from base 116. In this embodiment, the tools may include a dissecting tool, such as a cauterization tool 118 or a scraper, and a retracting member 120. For instance, cauterization tool 118 may be an electro-cautery hook or the like and retracting member 120 may be a radially expandable member, such as, e.g., a basket, surrounding cauterization tool 118. If retracting member 120 includes a basket, the basket may be of any suitable configuration. For instance, the basket may include one or more loops or legs, may be open or closed at one or more regions, and may be complete or partial. Portions of the basket need not be consistently spaced or sized, though they may be in some embodiments. The basket can include any suitable size, shape, or configuration.

This embodiment illustrates base 116 with an aperture 124 through which the tools may extend. Although the depicted embodiment depicts a single aperture 124, base 116 may include any suitable number of apertures 124. Aperture 124 provides a passageway from the sheath's lumen, allowing the cauterization tool to be translated between rest and deployed positions. Further, electrical connections or elongated supporting members may extend through the sheath's lumen, connecting cauterization tool 118 to the proximal end of medical device 100.

In other instances, base 116 may include apertures 124 for the retracting member 120 as well. In this case, both cauterization tool 118 and the retracting member 120 may be translatable between a rest position and a deployed position. Cauterization tool 118 and retracting member 120 may be able to switch positions independently, or they may be moved as a unit. For example, retracting member 120 may be deployed while cauterization tool 118 is in the rest position, or vice versa.

Alternatively, the tools can be fixedly coupled to base 116. In such a case, they may not be translatable. Instead, they may extend distally from end-effector 112 at all times.

The electro-cauterization tool may have a curved or bent distal portion 122 with an electrode at the distal tip. Electrical currents may be supplied to the bent distal portion 122, enabling the tool to burn or scar tissue for dissection. The curved distal portion 122 allows the operator to cauterize tissue at an angle to the longitudinal axis. In some instances, the bend angle of distal portion 122 may be adjustable, so that operators may configure the electrode's firing angle, as desired. Alternatively, distal portion 122 may be straight and may not have any provisions for angular displacement. The tool may be monopolar, requiring a ground pad, or bipolar, for instance. If bipolar, base 116 may act as an opposite pole to tool 118. Alternatively or additionally, alternate poles may be located on tool 118 and/or member 120.

Electrical connections may be provided to connect the proximal end of cauterization tool 118 with an internal or external power source. The power source may control the RF power provided to tool 118. Operators may use power controls present on handle 110 or on the external power supply to activate cauterization tool 118. If the power controls are present on handle 110, handle 110 may also include power means, such as a portable battery to activate cauterization tool 118. In addition, handle 110 may include a grounding pad for monopolar operation. Alternatively, the cauterization tool 118 may be integrated with a bipolar design having frequency opposite electrodes, eliminating the need for grounding pads.

In the deployed state, retracting member 120 may translate between a compressed state and an expanded state. In the compressed state, the diameter of retracting member 120 may be sufficiently small to engage and/or trap dissected tissue pieces or to grab a portion of the tissue sufficient to extract the rest of the tissue. In the expanded state, its diameter may be sufficiently large to radially push outward the tissue surrounding the cauterization tool, making space for the cauterization tool.

To shift between the compressed and expanded states, retracting member 120 may be self-expandable, or may be expanded by some external force. A self-expandable retracting member may be configured to transition to the expanded state without any assistance. To return self-expandable retracting member 120 into a compressed state, an external force may be required. Many techniques may be utilized to apply force on a self-expandable retracting member to keep or return retracting member 120 in the compressed state. Suitable materials to maintain a compressed state may include metal or polymer restraining rings, restraining sheaths, positional keying/locking features, or mechanical drive rods, e.g., to stretch or extend it to a collapsed configuration. Suitable materials to form self-expandable retracting member 120 may include polymers, composites, super-elastic and/or shape memory alloys, such as nitinol, stainless steel, etc. It will be understood that any other bio-compatible material now known or known in the future may be used to form the self-expandable member.

According to one technique, self-expandable retracting member 120 may be present within sheath 102 for deployment. Sheath 102 may exert a radially inward pressure on self-expandable retracting member 120, keeping it in the compressed state. Once retracting member 120 exits sheath 102, however, the pressure may be released, and self-expandable retracting member 120 may expand to its natural expanded state. In an embodiment, sheath 102 may include reinforcements, such as braids or coils, to strengthen the walls. It will be understood that in such situations, the material and thickness of sheath 102 may be selected such that it applies a greater force on self-expandable retracting member 120 than the force exerted by the member on sheath 102. In some embodiments, if the sheath material is too thin or too elastic, for example, it may not be sufficient to hold self-expandable retracting member 120 in the compressed state and the member may expand within the sheath itself. Alternatively, if sheath 102 is too rigid or thick, it may not be able to traverse the circuitous path within a patient's body, causing injury. Therefore, it may be often preferred to select a suitable material and thickness keeping both aspects in mind.

According to another technique, one or more pull wires (not shown) may be utilized. Pull wires may be attached to the expandable member's distal end or proximal end. When a pull wire is pulled in a certain axial direction (distally or proximally), it may place a tensile force on the expandable member, stretching it longitudinally and compressing it radially. When the pull wire is released, the tensile force is released permitting, the member to expand. For example, if the pull wire is attached to the member's distal end, pulling the wire distally may elongate (compress) the member, and releasing the pull wire, may release the force on the member, expanding it. Moreover, means to pull, push, or release the pull wire may be configured in the device's handle 110 allowing operators to easily expand or compress the member, as required.

In some embodiments, movement of handle 110 may correspond with expansion of member 120. The ratio of movement between handle 110 and member 120 may be of any suitable ratio, for instance, a direct 1:1 ratio, or movement of handle 110 may cause a comparatively smaller movement of member 120, or movement of handle 110 may cause a comparatively larger movement of member 120. In some embodiments, handle 110 may include markings to indicate to a user the size, shape, or directional movement of member 120. Alternatively, the actuation means may be present external to handle 110. Further, any suitable reinforcement structure, for example, a coil and/or braiding, may be used.

Non self-expanding retracting members 120 may include an external force to bring the retracting member into an expanded state. In some cases, these members may stay in the expanded state as long as the external force exists and return to the compressed state once the force ceases to exist. Other members 120 may be able to maintain the expanded state even after the external force is removed. An opposite force may then be included in such devices to bring them back into the compressed state. Expansion means, such as, for example, an inflatable balloon, can be used to expand such retractable members 120 by placing an outward radial force on the member. Such expansion means (not shown) may include balloons inflated by fluids or dilators. Elastic or plastic deformation of the expandable member or a combination thereof may also be contemplated. Other such inflating means may also be utilized without departing from the scope of the present disclosure. For example, means such as springs or levers may be utilized to expand member 120. Similarly, member 120 itself may be configured to include pivotal structures connected to one another. For instance, member 120 may be formed of multiple wires connected to one another along pivotal joints (not shown). An outward force on the pivotal joints may expand the various wires connected to the joint, expanding retracting member 120.

In another embodiment, expansion may be induced by pulling the distal end of retracting member 120 proximally, while holding the proximal end steady. Similarly, the proximal end may be compressed axially, while holding the distal end fixed. In some embodiments, both the proximal and distal ends of retracting member 120 may be pushed towards each other for expansion purposes.

The expansion of retracting member 120 may be limited so that it does not cause damage to the cavity. For example, excessive expansion or expansion force may damage internal cavities. To avoid such large expansion diameters, member 120 may include visualization aids, such as cameras or fluorescent dyes, to visualize the extent of expansion. Further, member 120 may include a force or expansion-limiting component that prevents member 120 from expanding beyond a certain limit. In some instances, the expansion limit may be set during manufacture. For example, operators may know the average body cavity sizes, and they may ensure the member does not expand beyond the average lumen size.

In some embodiments, this device may operate without sheath 102, for instance, if retracting member 120 can be otherwise expanded.

Figure 2A:
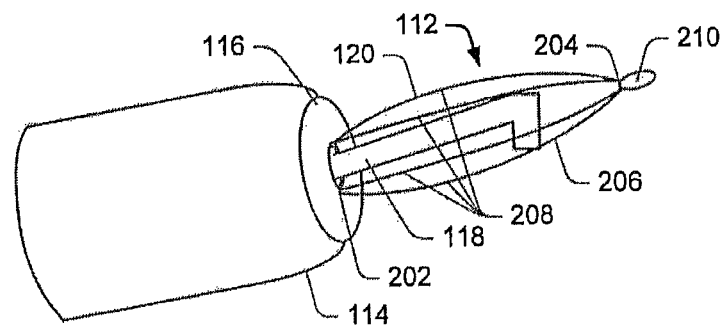
FIG. 2A is a perspective view depicting an exemplary end-effector of the integrated medical device of FIG. 1 in a compressed state.
Figure 2B:
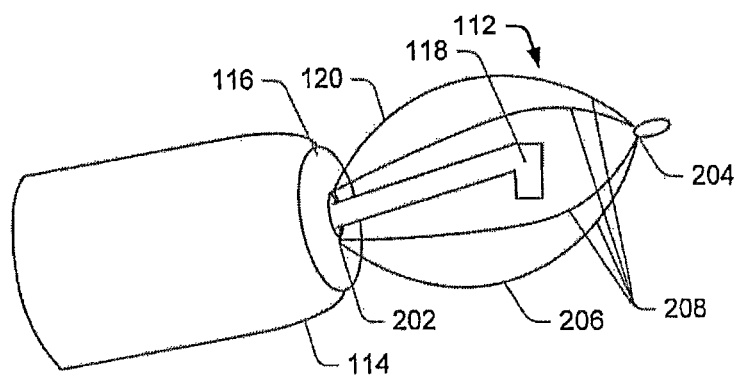
FIG. 2B is a perspective view of the end-effector shown in FIG. 2A in an expanded state.

FIGS. 2A-2B are perspective views of an exemplary end-effector 112. More particularly, FIG. 2A illustrates end-effector 112 with retracting member 120 in the compressed state, and FIG. 2B illustrates end-effector 112 with retracting member 120 in an expanded state. Here, end-effector 112 includes cauterization tool 118 and retracting member 120, which has a proximal end 202 and a distal end 204. Retracting member 120 is configured as a basket 206 having multiple legs 208. Legs 208 are joined together along the longitudinal axis at the proximal and distal ends of the member.

The shielding or retracting member may surround cauterization tool 118 at any desired angle, such as 360 degrees or less. This allows tool 118 (hook, grasper, or dissector, for examples) to operate, while retracting member 120 retracts tissue on the back side of tool 118. Additionally, as a shielding design, the shielding members may be 360 degrees around or less, to shield tool 118 for safe passage through a working channel. In one embodiment, retracting member 120 may include two independent members, and among these, one member may advance and the other may retract, or a combination thereof. Alternatively, at least one of the members may rotate around the distal end for shielding or retracting purposes.

In the illustrated embodiment, multiple legs 208 axially extend from proximal end 202 to distal end 204 of retracting member 120. In other embodiments, however, legs 208 may follow a spiral or helical path from the proximal end to the distal end. It will be understood that other basket configurations are also within the scope of the present disclosure. In addition, the number of legs 208 may vary based on application. For example, two, three or more legs may extend from proximal end 202 to distal end 204. In all basket embodiments, however, legs 208 may remain substantially parallel to the longitudinal axis in the compressed state, and may radially expand in the expanded state. For the embodiment including helical legs 208, the rotation of helical legs 208 relative to the cap-like structure 114 may result in expansion and/or compression of retracting member 120.

Each leg 208 may be formed of a single wire extending from the proximal end to the distal end. Alternatively, legs 208 may be formed of multiple wires, e.g., twisted or braided along the length of the retracting member. Moreover, multi-wire legs 208 may extend along the entire length of the retracting member and the sheath, or only the length of the retracting member. In other embodiments, portions of legs 208 may be formed of single wires, while other portions may be formed of multiple wires. In yet other embodiments, the thickness of the wires may be uniform along the length of the legs. Alternatively, the wires may be thicker in the middle and thinner at the proximal and distal portions of legs 208, or vice-versa. Alternatively, legs 208 may be formed using stamping sheet metal or molded, extruded, or slitting a polymer such as a malecot geometry. In some embodiments, a mesh may extend between or around adjacent legs 208. This mesh may be flexible, elastic, and/or deformable for instance, and/or may be formed of flexible, elastic, and/or deformable materials. In other embodiments, the mesh may be more rigid, or include both flexible and rigid portions. The mesh may be formed of any suitable material, for instance, a metal or a polymer. The mesh may be fixedly and/or slideably coupled to one or more of the legs and/or a distal end of retracting member 120 or shaft 102. Legs 208 and/or the wires may have any suitable cross-sectional shape, for example, round, oval, rectangular, D-shaped, triangular, or flat.

Retracting member 120 may further include a blunt tip 210 (FIG. 2A) that may aid in dissecting tissue, while causing minimum damage to surrounding tissue during expansion. Further, blunt tip 210 may be in the form of a small cap covering and may secure the distal ends of legs 208. In addition to securing the distal ends of legs 208, blunt tip 210 may serve as a backstop for a stone or tissue during a fragmentation procedure. Blunt tip 210 may include metals, polymers, ceramics, or any other suitable biocompatible material. To aid in visualization and placement, blunt tip 210 may include radiopaque markers allowing operators to help discern the exact location of the distal end of retracting member 120 or may comprise radiopaque materials. Further, antibacterial and/or antibiotic coatings may be applied to blunt tip 210 to prevent bacterial infection during the procedure. Blunt tip 210 may also extend from the legs as a leading atraumatic flexible guide.

In an alternate embodiment, retracting member 120 may include no tip. For example, each leg 208 may be a substantially circular structure wrapped around each other at their distal tip. In such embodiments, legs 208 may be glued or knotted at the distal end to form a basket-shaped member 120.

By radial expansion, retracting member 120 may push outward on surrounding tissue, and may provide space for cauterization tool 118 to cauterize the required tissue. The degree of expansion and the strength of legs 208 may determine the cavity area created by retracting member 120. For example, if legs 208 have a very small diameter, they may not be able to push the tissue too far, as the force exerted by the legs on the tissue may be comparable to the force exerted by the tissue on the legs. Alternatively, if the diameter of the legs is too large, they may be able to apply a greater force on the tissue, pushing it further away from the procedure site. In each of the embodiment, the spacing between legs 208 may be enough for cauterization tool 118 to extend out of the retracting member. Alternatively, cauterization tool 118 may be positioned proximally or distally to the retracing member to gain access to the tissue.

Once cauterization tool 118 has dissected the required tissue, the cauterization tool may be retracted into the sheath and retracting member 120 may be compressed, such that it holds the dissected tissue within the legs. Subsequently, retracting member 120 may be withdrawn, or the entire endoscopic device 100 may be retracted proximally to remove the dissected tissue.

In another embodiment, legs 208 may have a sharp cutting edge (not shown), such that the expansion member may dissect tissue during expansion. In some embodiments, the operator may rotate sheath 102, in turn rotating expandable member 120, allowing it to behave as a scoring tool. In such an embodiment, it may be preferable to control the degree of expansion, so that the operator may control tissue dissection. According to one control technique, the operators may slowly release pull wires holding the member compressed, thereby releasing the tensile force in a controlled fashion. In some embodiments, legs 208 may conduct electricity. For instance, upon contact with a lumen wall or tissue, legs 208 may be able to cut or cauterize the lumen or tissue when energized.

In other cases, legs 208 may include suitable coatings, such as antibacterial coatings, lubricious materials, drug-releasing agents, or radiopaque markers. It will be understood that these, or any other suitable medical device coating, may be applied to legs 208 without departing from the scope of the present disclosure.

Figure 3A:
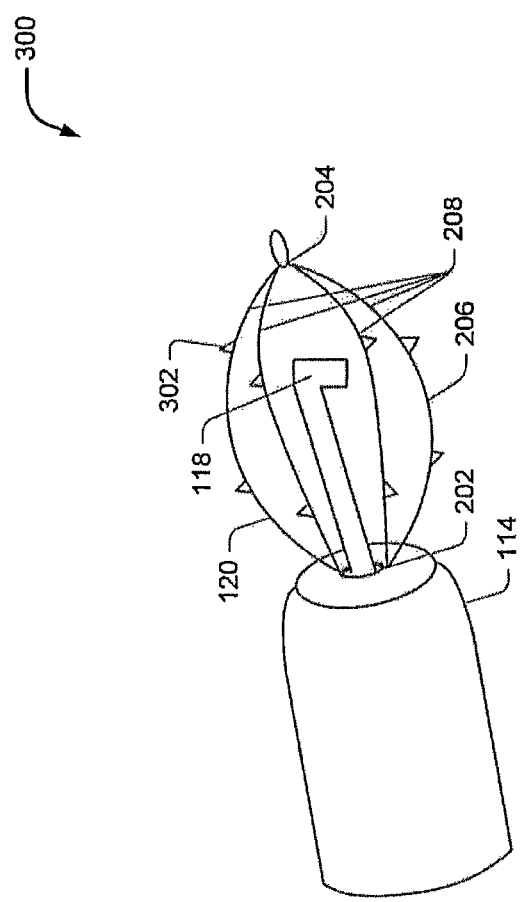
FIGS. 3A-3C are perspective views of alternate end-effectors.
Figure 3B:
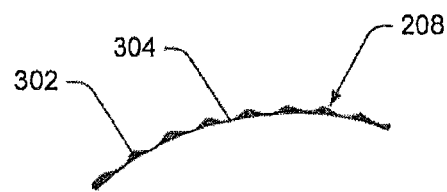
Figure 3C:
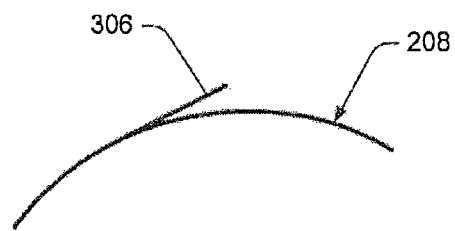

FIGS. 3A-3C illustrate another exemplary end-effector 300, according to a further embodiment of the present disclosure. The illustrated embodiment depict end-effector 300 having geometrical structures, such as projections, that facilitate grasping of surrounding tissue upon expansion and prevent any inadvertent displacement during the procedure. In FIG. 3A, the outer surface of legs 208 may include one or more projections 302 in the form of barbs, wires, or hooks, or any other suitable geometric configurations.

FIG. 3B depicts end-effector 300 having notches 304 formed on the outer surface of legs 208, leaving a portion of the surface to act as projections 302. Alternatively, projections 302 may be separate members attached to the outer surface of legs 208 using known mechanisms such as adhesives, molding, etc.

Other embodiments of legs 208 having projections may be contemplated. None, some, or all of legs 208 may include projections 302. In some instances, projections 302 may extend from the surface of the legs 208. In other instances, projections 302 may be retractable into lumens present in the legs, or they may lie along the length of legs 208 in a rest state and pivot away from legs 208 once endoscopic device 100 is in position. FIG. 3C depicts one such embodiment. Here, the outer surface of legs 208 may include cut-out section 306. Bending or expansion of legs 208 along the cuts may cause section 306 to protrude out, forming a projection.

In other embodiments, the pivoting projections may automatically extend at an angle to legs 208 when the legs expand. Alternatively, legs 208 or handle 110 may include an actuation mechanism to pivot projections 302 to deploy them when desired. It is understood that this disclosure describes limited examples of the position and actuation mechanisms of projections 302, but various other positions and actuation techniques exist, and any of these may be utilized without departing from the scope of the present disclosure.

Once projections 302 hold onto the surrounding tissue, cauterization tool 118 may be translated between a retracted and a deployed position, so that it may cauterize tissue at one or more locations. When cauterization is complete, projections 302 may be retracted, and retracting member 120 may be compressed to trap and/or retract the dissected tissue. In some embodiments, member 120 and/or base 116 may function as an opposite pole or as a ground.

Alternatively, or in addition, projections 302 may be present on the inward facing surfaces of legs 208. Because these projections are inward facing, they may grasp the dissected tissue when retracting member 120 is compressed, preventing the tissue from slipping out of the basket during retraction. The number and positions of the projections may vary considerably without departing from the disclosure's scope.

Figure 4:
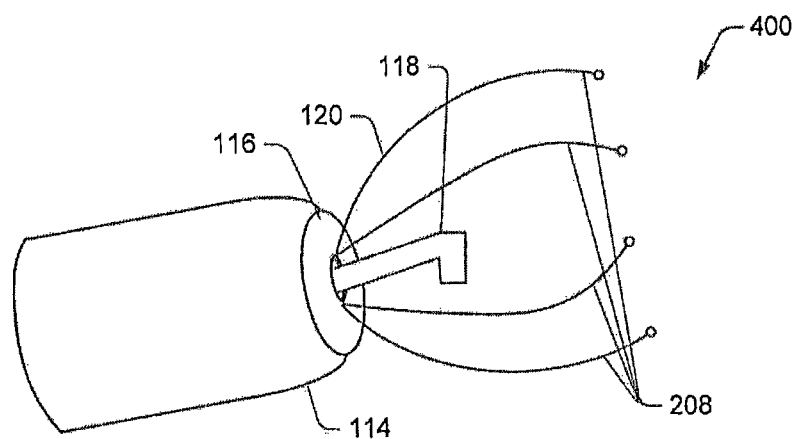
FIG. 4 is a perspective view of an exemplary end-effector with a distally expanding retracting member.

FIG. 4 is a perspective view of another exemplary end-effector 400 with a distally flaring extendable or retractable retracting (tissue) member 120. Legs 208 flare distally, instead of being joined at the distal end. In the illustrated embodiment, legs 208 flare in a generally concave fashion. In other instances, legs 208 may flare, e.g., in a convex fashion, concave conical fashion, pyramid fashion, or multiple bend fashion. In the compressed state, legs 208 may be close to the longitudinal axis, and in the expanded state, legs 208 may radially flare at the distal end. Further, the distal tips of legs 208 may be blunt to cause fewer traumas to surrounding organs and tissue.

The distal flare may separate tissue surrounding cauterization tool 118, allowing end-effector 400 to advance in narrow cavities and to make space for cauterization tool 118 to dissect tissue once end-effector 400 is in the desired location.

Figure 5:
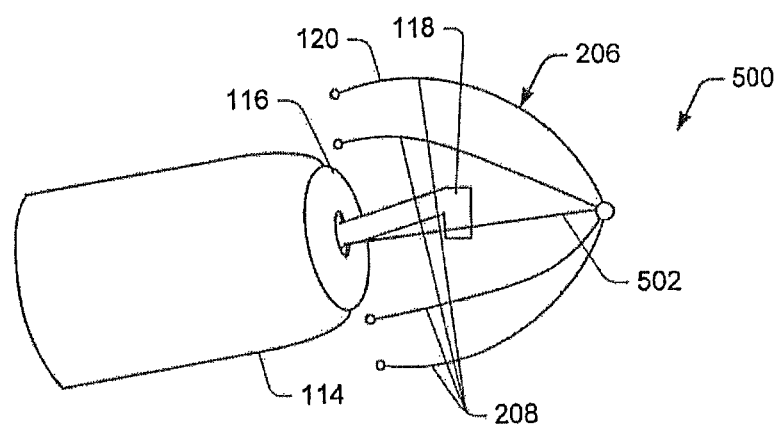
FIG. 5 is a perspective view of an exemplary end-effector with a proximally expanding retracting member.

FIG. 5 illustrates an alternate end-effector embodiment 500, where legs 208 are joined at the distal end and flare out at the proximal end. To this end, a central leg 502 may extend from the end-effector 500 to the retracting member's distal end. The other radial legs 208 may be joined to the distal end of this central leg 502. When the expandable member is compressed, the proximal end of legs 208 may rest close to the longitudinal axis, and when the member is expanded, the proximal ends may flare out radially.

The proximally flaring basket may protect surrounding tissue from cauterization tool 118 during dissection and may separate the dissected tissue from the surrounding tissue with the umbrella-shaped basket 206. When retracting member 120 is compressed for tissue withdrawal, the proximal tips of the legs may rest against base 116, so that they do not engage with the body cavity during device extraction.

In addition to the embodiments described in FIGS. 2-5, expandable member 120 may also include a trailing feature or arms that flare out to keep the dissected tissue separated.

Figure 6A:
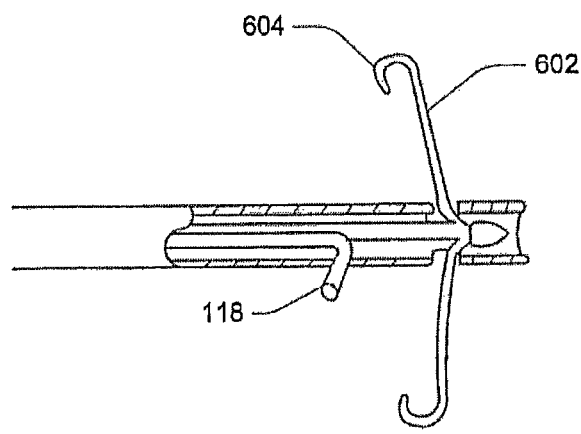
FIGS. 6A-6D illustrate alternate embodiments of the end-effector having a trailing feature.
Figure 6B:
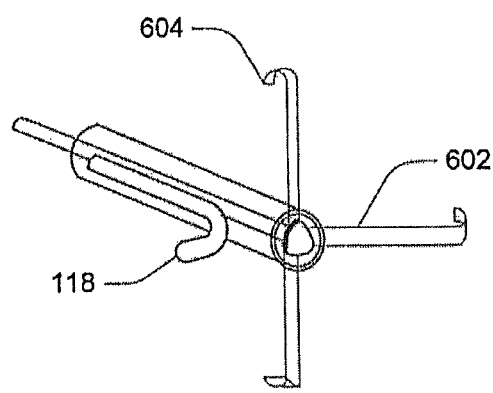
Figure 6C:
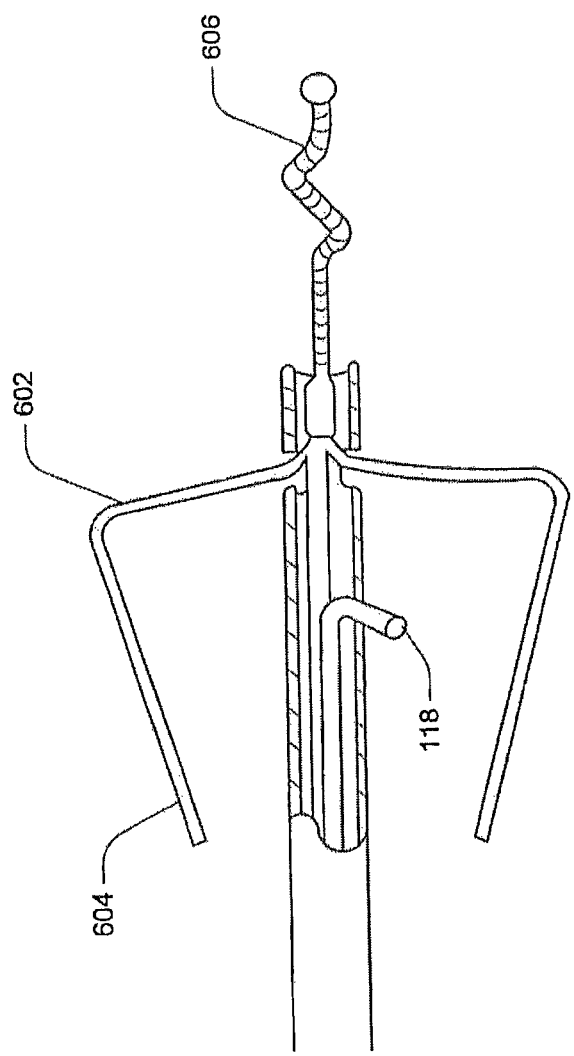

FIGS. 6A-6C illustrate different configurations of the trailing feature. Apart from the different elements of the end-effector already described, an end-effector 112 may include trailing features 602, which may include one or more arms extending in a radial direction from a distal portion of end-effector 112. Arms 602 may remain in a collapsed state along the length of end-effector 112 during insertion or retraction. Once deployed, arms 602 may flare out to assume an expanded configuration using known mechanisms such as a spring. In some embodiments, arms 602 may be self-expanding. It other embodiments, arms 602 may be expanded by any suitable mechanism known in the art.

In addition, the distal ends of arms 602 may include atraumatic ends 604. As shown, ends 604 of arms 602 may be, e.g., curved (as shown in FIG. 6A), bent (FIG. 6B), or the ends may extend proximally along the length of the end-effector at an angle converging towards end-effector 112.

In some embodiments, arms 602 extend radially to hold dissected tissue separated. In addition, the distal ends 604 of arms 602 may be bent or curved or may include other geometrical features to not only engage the surrounding tissue, but also prevent damaging the tissue. Ends 604 may also assist in maintaining tissue in a desired position.

In some embodiments, trailing features 602 may include an additional extension 606 (FIG. 6C) extending distally in a direction substantially parallel to the longitudinal axis of elongate member 102. As shown, extension 606 may include curves or bends along its length. In one embodiment, extension 606 may remain collapsed along its bends during insertion, and once the medical device is deployed, extension 606 along with trailing features 602 may expand. These trailing features may engage the surrounding tissue and expansion of the features may result in tissue separation.

Figure 6D:
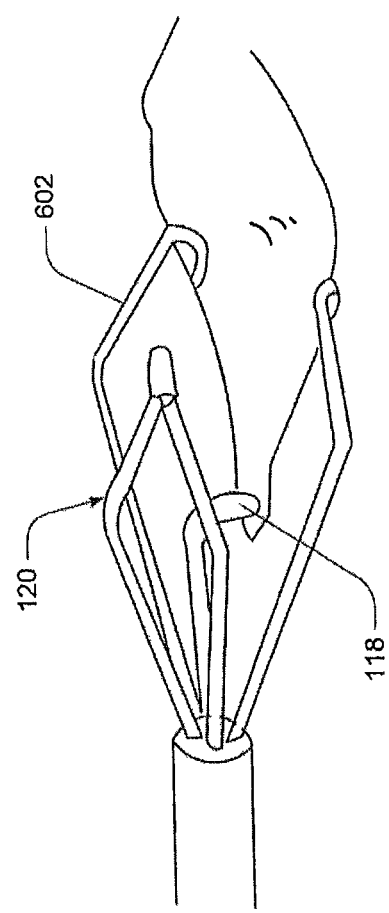

In addition, trailing features 602 may be positioned proximally or distally to retracting member 120. In one embodiment, retracting member 120 may expand and may remain proximal relative to trailing feature 602, as shown in FIG. 6D. As shown, trailing features 602 may expand and engage the target tissue, while retracting member 120, being positioned proximal to trailing feature 602, may provide further tissue tension. In this configuration, cauterization tool 118, for example a hook, may operate to perform a desired procedure, such as tissue removal.

In some embodiments, retracting member 120 may also assume a mesh-type configuration that may translate between an expanded state and a compressed state. In the compressed state, retracting member 120 may remain collapsed. For example, collapsed retracting member 120 may assume a hollow cylindrical shape having a diameter similar to that of sheath 102. Once deployed, retracting member 120 may expand radially to assume a desired shape, such as, e.g., cone, disk, saucer, or doughnut shapes.

Figure 7A:
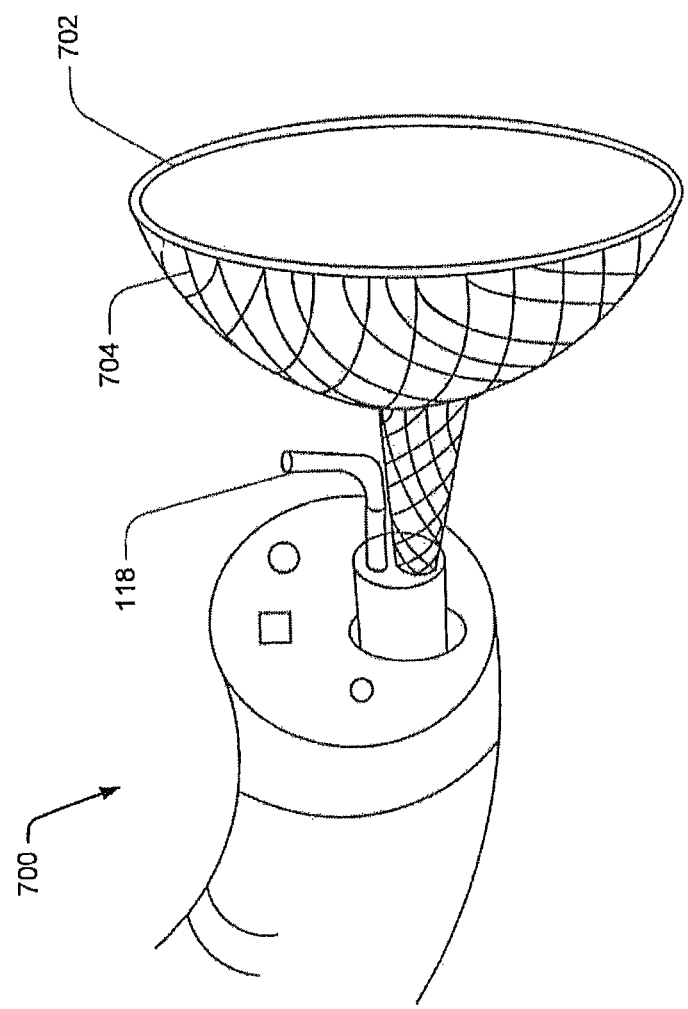
FIGS. 7A and 7B are perspective views of another exemplary end-effector having a mesh-type retracting member.
Figure 7B:
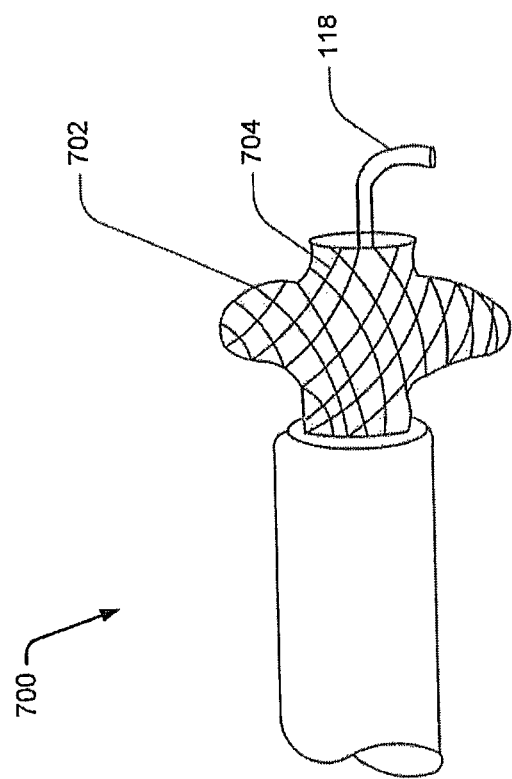

FIGS. 7A and 7B illustrate two configurations of alternate end-effector embodiments 700 having a mesh-type retracting member 702 and cauterization tool 118. Similar to the retracting member 120 of FIG. 2, mesh-type retracting member 702 may translate between an expanded state and a compressed state. The expanded shape and configuration of retracting member 702 may vary. For example, as shown in FIG. 7A, retracting member 702 may assume a conical shape. In comparison, as shown in FIG. 7B, retracting member 702 may assume into a doughnut-shaped member.

Mesh-type retracting member 702 and cauterization tool 118 may be positioned such that the two elements operate independently or without interference. In general, retracting member 702 may be spaced from cauterization tool 118, providing visualization to tool 118 while retracting surrounding tissue. In FIG. 7A, retracting member 702 may expand at a position distally from cauterization tool 118. While in FIG. 7B, a doughnut-shaped retracting member 702 may include an opening for allowing passage of cauterization tool 118 to a distal location. The opening may assume different configurations and may allow cauterization tool 118 to extend from the retracting member in any desired angle or position. Different configurations of retracting member 702 and cauterization tool 118 are contemplated.

In some embodiments, retracting member 702 may be formed of multiple filaments 704 arranged generally in two sets of parallel helices wound in opposite directions about a common longitudinal axis. The filaments may intersect each other in an overlapping pattern at multiple interstices. These interstices may permit two filament sets to move with respect to each other, allowing retracting member 702 to radially expand when subjected to a compressive force and radially shrink when subjected to a tensile force. The ends of each of the filaments may be constrained to prevent the filaments from fraying or unraveling.

In other embodiments (not shown), filaments 704 may be arranged in different configurations. For example, retracting member 702 may be formed by winding one set of helices in the same direction. Alternatively, two helical sets may be wound in one direction and a third set may be wound in a second direction. Any number of winding patterns and configurations are possible.

The shape, thickness, or other characteristics of filaments 704 may also vary. For example, filaments 704 may include multi-filar threads woven together to form filaments having a generally round shape. Alternatively, other filament configurations may be employed, such as round wire, flat ribbon, threads, fibers, monofilament, multi-filament, or combinations thereof. Filament thickness may vary, providing different resistance to radial expansion as retracting member 702 is inserted into a patient's body; in general, the larger the filament size, the greater the resistance to radial expansion.

The expandability of retracting member 702 may also be, in part, attributable to the material composition of the filaments. Some exemplary materials include, e.g., polymers, super-elastic alloys, shape-memory materials, metals, metal alloys, metal-polymer composites, or metal-metal composites. Shape-memory and spring-wire materials may be biased to assume an expanded state and restrained to a retracted shape. Retractor actuation may not require tensile or compression forces. Elastomeric materials, such as plastics, may impart flexibility to the elongate member. Examples of suitable metals or metal alloys may include, e.g., stainless steel, platinum, tungsten alloy, and nickel-titanium alloy.

In some embodiments, a biocompatible polymer material, such as silicone, may coat at least some of the filaments. A complete sheath may be formed so that dissected tissue does not pass through gaps between the filaments.

In the expanded state, retracting member 702 may push the surrounding tissue apart to form space for cauterization tool 118 to advance and dissect tissue. In the compressed state, retracting member 702 may hold the dissected tissue for retraction.

The medical devices and end-effectors described in FIGS. 1-7 may be employed to perform a method for manipulating tissue from within a body of a patient. For example, one or more medical devices and end-effectors may be introduced in a body of a patient through an exemplary medical device, such as, e.g., an endoscopic device, a guide tube, or an introducer. Once in the endoscopic device, medical device 100 may be urged distally until the distal end of medical device 100 protrudes from the distal end of the endoscopic device. If end-effector 112 is within sheath 102 during the transportation, it may be deployed when medical device 100 is positioned proximate the desired location. Subsequently, retracting member 120 may be expanded to increase the cavity size. Next, cauterization tool 118 may be activated and configured to achieve a desired firing angle for energizing tissue. The tool may be activated to cauterize tissue once the angle is adjusted. Cauterization tool 118 may subsequently be retreated in sheath 102 and retracting member 120 may be compressed to hold the dissected tissue. Medical device 100 may then be retracted proximally and removed from the endoscopic device.

Medical device 100 might be used to carry out a variety of medical or non-medical procedures, including surgical and diagnostic procedures in a wide variety of bodily locations. For example, mucosal resection or ablation of numerous body organs, such as esophagus, stomach, bladder, or the urethra could be accomplished using the method discussed above. In addition, at least certain aspects of the aforementioned embodiments may be combined with other aspects of the embodiments, or removed without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. An end-effector for a medical device, the end-effector comprising:
   a cauterization tool; and
   a retracting member having:
      a proximal end,
      a distal end,
      a plurality of legs extending from the proximal end to the distal end,
      a central longitudinal axis extending through a radial center of the retracting member, the retracting member being movable between a radially collapsed configuration and a radially expanded configuration,
      at least one barb, wire, or hook extending from a respective leg of the plurality of legs toward the central longitudinal axis, the at least one barb, wire, or hook being configured to grasp dissected tissue when the retracting member is in the radially compressed configuration, and
      one or more first projections extending radially outward from one or more of the plurality of legs and in a direction away from the central longitudinal axis, wherein each of the one or more first projections is movable relative to the leg from which it extends, each of the plurality of legs includes a proximal end and a distal end, and at least one of the proximal ends and the distal ends of the plurality legs are joined together, the plurality of legs are configured to transition between the radially collapsed configuration and the radially expanded configuration, and the cauterization tool is movable within a volume radially inward of all of the plurality of legs when the plurality of legs are in the radially expanded configuration.

2. The end-effector of claim 1, wherein the distal end of the retracting member includes an atraumatic tip.

3. The end-effector of claim 1, wherein the proximal ends of the plurality of legs are joined together at the proximal end of the retracting member, and the distal ends of the plurality of legs are joined together at the distal end of the retracting member.

4. The end-effector of claim 3, wherein the retracting member is self-expandable.

5. A multi-functional medical device, comprising:
   a sheath having a proximal end, a distal end, and a lumen extending therebetween; and
   an end-effector slidably disposed within the lumen of the sheath, the end-effector comprising:
      a tool configured to dissect tissue, wherein the tool includes a distal portion and a tool longitudinal axis, wherein the distal portion is bent relative to the tool longitudinal axis at a bend angle, and the bend angle is adjustable; and
      a retracting member having a plurality of legs disposed about the tool, wherein each of the plurality of legs includes a lumen, a sharp cutting edge, and at least one retractable projection, the at least one retractable projection is a barb, wire, or hook, each retractable projection extends radially outward from a respective leg of the plurality of legs while in a first configuration, and each retractable projection is contained within the lumen of the respective leg of the plurality of legs in a second configuration, wherein the retracting member further includes:

a central longitudinal axis extending through a radial center of the retracting member, the retracting member being movable between a longitudinally-extended and radially-compressed orientation, and a longitudinally-compressed and radially-expanded orientation, and one or more grasping projections extending from a respective leg of the plurality of legs toward the central longitudinal axis, the one or more grasping projections being configured to grasp dissected tissue when the retracting member is in the longitudinally-extended and radially-compressed orientation, wherein the one or more grasping projections includes at least one barb, wire, or hook;

a mesh disposed between at least some circumferentially adjacent legs of the plurality of legs.

6. The multi-functional medical device of claim 5, wherein the tool is a cautery hook.

7. The multi-functional medical device of claim 5, wherein the retracting member is a self-expandable partial basket.

8. The multi-functional medical device of claim 5, wherein the plurality of legs are coupled to one another at the distal end of the retracting member and at the proximal end of the retracting member.

9. The multi-functional medical device of claim 5, wherein the distal end of the retracting member includes an atraumatic tip.

10. The medical device of claim 5, further including a pull wire coupled to a proximal end of the retracting member or a distal end of the retracting member, wherein the pull wire is movable in a longitudinal direction to transition the retracting member between the longitudinally-extended and radially-compressed orientation, and the longitudinally-compressed and radially-expanded orientation.

11. The medical device of claim 10, wherein the medical device is configured to deliver bipolar energy, and either the tool and a distal end of the end effector are configured as opposite poles, or the tool and one of the plurality of legs are configured as opposite poles.

12. A medical device, comprising:
an end-effector including:
a tool configured to cauterize tissue; and
a retracting member having a plurality of legs disposed about the tool and a central longitudinal axis extending through a radial center of the retracting member, the retracting member being movable between a longitudinally-extended and radially-compressed orientation, and a longitudinally-compressed and radially-expanded orientation, wherein each of the plurality of legs includes a lumen, at least one retractable projection, and at least one barb, wire, or hook extending from a respective leg of the plurality of legs toward the central longitudinal axis, the at least one barb, wire, or hook being configured to grasp dissected tissue when the retracting member is in the longitudinally-extended and radially-compressed configuration, wherein each retractable projection extends radially outward from a respective leg of the plurality of legs in a direction away from the central longitudinal axis while in a first configuration, each retractable projection is contained within the lumen of the respective leg of the plurality of legs in a second configuration, and the tool is movable relative to the retracting member while each retractable projection remains in the first configuration.

13. The medical device of claim 12, wherein the end-effector includes a cap, and the cap includes a base with a single aperture.

14. The medical device of claim 12, further including a pull wire coupled to a proximal end of the retracting member or a distal end of the retracting member, wherein the pull wire is movable in a longitudinal direction to transition the retracting member between the longitudinally-extended and radially-compressed orientation, and the longitudinally-compressed and radially-expanded orientation.

15. The medical device of claim 12, wherein the medical device is configured to deliver bipolar energy, and the tool and a distal end of the end effector are configured as opposite poles.

16. The medical device of claim 12, wherein the medical device is configured to deliver bipolar energy, and the tool and one of the plurality of legs are configured as opposite poles.

17. The medical device of claim 12, wherein the tool includes a distal portion and a tool longitudinal axis, wherein the distal portion is bent relative to the tool longitudinal axis at a bend angle, and the bend angle is adjustable.

18. The medical device of claim 12, further including a mesh disposed between at least some circumferentially adjacent legs of the plurality of legs.

19. The medical device of claim 18, wherein each leg of the plurality of legs includes a sharp cutting edge.

* * * * *